United States Patent [19]

Spitler

[11] Patent Number: 5,005,374
[45] Date of Patent: Apr. 9, 1991

[54] THERMAL WRAPS

[75] Inventor: Michael L. Spitler, Phoenix, Ariz.

[73] Assignee: Chillynex Corporation, Tempe, Ariz.

[21] Appl. No.: 515,226

[22] Filed: Apr. 27, 1990

[51] Int. Cl.$^5$ ............................................. F25D 23/12
[52] U.S. Cl. ..................................... 62/259.3; 62/372;
   62/457.2; 62/457.3; 62/530; 128/380; 128/402
[58] Field of Search ................... 62/457.4, 457.2, 530,
   62/372, 259.3, 457.8; 128/380, 402, 403

[56] References Cited

U.S. PATENT DOCUMENTS

| | | | |
|---|---|---|---|
| 296,432 | 4/1884 | Moebius | 62/457.4 X |
| 2,216,330 | 10/1940 | Stover | 62/372 |
| 4,204,543 | 5/1980 | Henderson | 128/403 X |
| 4,326,533 | 4/1982 | Henderson | 128/402 |
| 4,338,795 | 7/1982 | House, Jr. | 62/457.8 |
| 4,413,481 | 11/1983 | Thomas | 62/457.4 X |
| 4,676,247 | 6/1987 | Van Cleve | 62/530 X |
| 4,831,842 | 5/1989 | Kelley et al. | 62/457.4 |
| 4,832,030 | 5/1989 | De Canto | 128/380 |

Primary Examiner—Lloyd L. King
Attorney, Agent, or Firm—Don J. Flickinger; Jordan M. Meschkow

[57] ABSTRACT

A thermal wrap includes a fabric band having a thermally insulating outer layer and a non-insulating inner layer. A cavity is formed between the two layers for receiving a flexible cold pack containing deionized water and a chemical freezing agent. In one embodiment, the fabric band is in the form of a collar to be worn about the individual's neck or other body part. In another embodiment, the fabric band is in the form of a jacket for surrounding a beverage container such as a wine bottle.

20 Claims, 2 Drawing Sheets

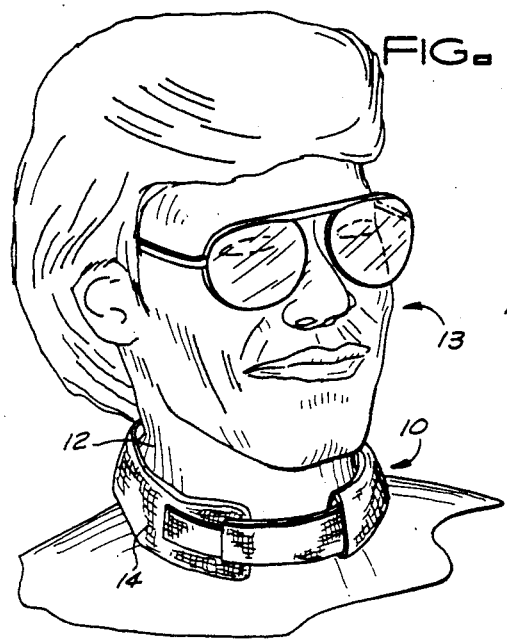
FIG. 1
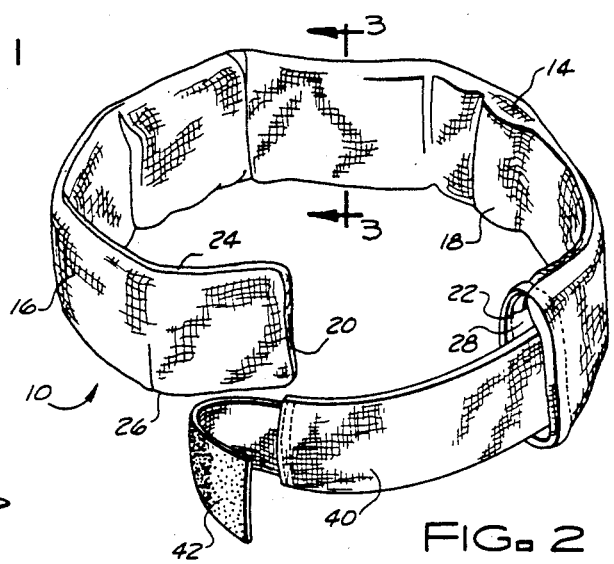
FIG. 2
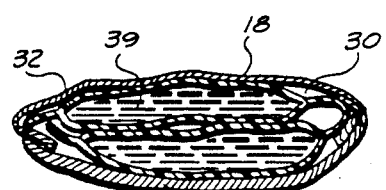
FIG. 3
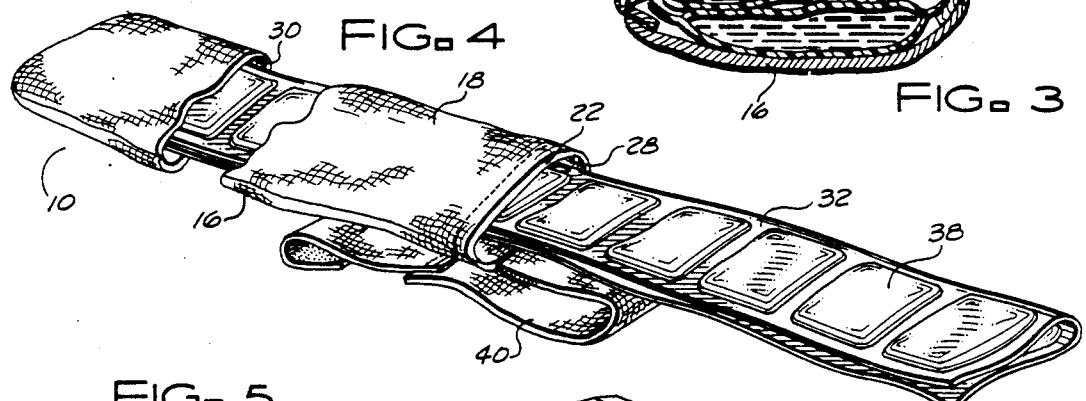
FIG. 4
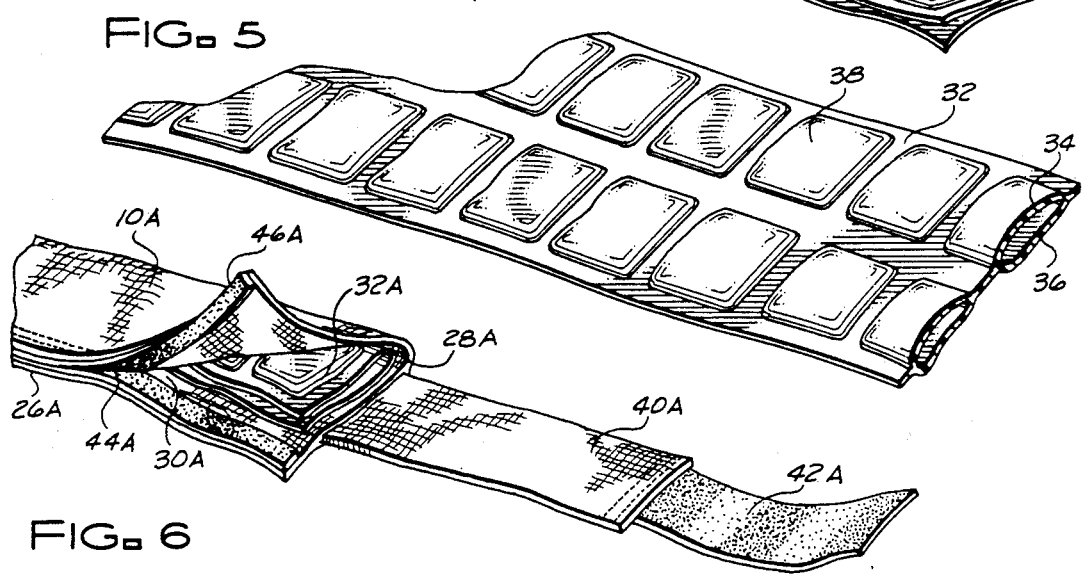
FIG. 5
FIG. 6

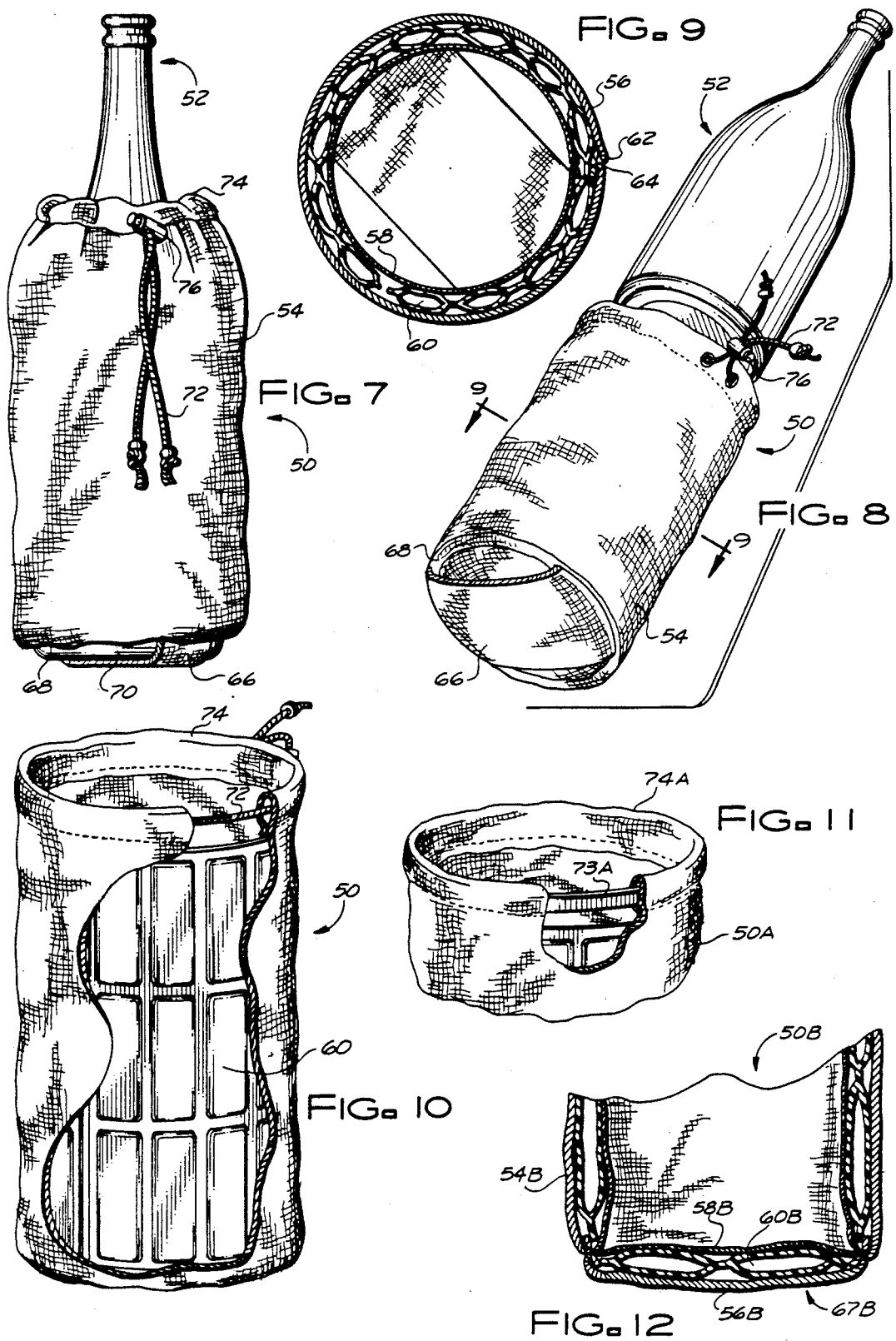

THERMAL WRAPS

BACKGROUND OF THE INVENTION

1. Field of the Invention

This invention relates to the art of thermal wraps.

More particularly, this invention relates to wraps for containing hot or cold pack inserts.

In a further and more specific aspect, the instant invention concerns thermal wraps for keeping an individual cool or for chilling a product such as a beverage.

2. Description of the Prior Art

The use of thermal wraps to reduce the pain of an injured body part or to keep an individual cool during strenuous exercise such as jogging is generally well known. These thermal wraps are commonly in the form of fabric collars or cuffs having cavities for containing ice, wet towels, or cold pack inserts which are capable of maintaining a cold temperature over long periods of time.

Those thermal wraps which contain ice tend to become soggy and messy as the ice melts, thus reducing the wearer's level of comfort. In addition, the need to frequently replace the melted ice is an inconvenience which most users would like to avoid. Similar problems exist with wraps using wet towels, which drip if they are too wet and ineffective if they are too dry.

As a result, both of the above types of wraps have lost favor over the years and have been replaced with wraps containing dry packs which rely on chemical reactions or freezing agents to remain at low temperatures for prolonged periods. Despite their tendency to remain dry, however, even these newer wraps have drawbacks which have prevented them from attaining widespread acceptance. For instance, most of the prior art wraps include rather complex interior structures for maintaining the cold pack in a central position. These complex structures require time-consuming manufacturing procedures and increase the overall cost of the product. In addition, the wraps are generally not washable, and thus become dirty and perspiration-soaked after several wearings, especially if the wearer engages in vigorous physical activity.

In addition to the various body-cooling wraps described above, there are several devices available for chilling inanimate objects such as foods and beverages. One well-known chilling device is the common ice bucket used for chilling wine and other drinks, both canned and bottled. The simplest type of ice bucket is a rigid receptacle having a continuous outer wall which forms an annular space around the bottle or other container to be chilled. The annular space is filled with ice.

One problem with the conventional ice bucket is the mess and inconvenience associated with the melting ice. Another problem is the size of the bucket, which makes it difficult to store and unwieldy to transport from place to place.

It would be highly advantageous, therefore, to remedy the foregoing and other deficiencies inherent in the prior art.

Accordingly, it is an object of the present invention to provide improved thermal wraps for cooling an individual or for chilling beverages and other products.

Another object of the invention is the provision of an apparatus for retaining a cold pack insert.

And another object of the invention is to provide an iceless thermal wrap which cools an individual or a product without dripping or condensing after several hours of use.

Still another object of the invention is the provision of a washable thermal collar.

Yet another object of the invention is the provision of a thermal collar with a removable cold pack insert.

Yet still another object of the invention is the provision of an adjustable thermal collar which can accommodate body parts of many different sizes.

And a further object of the invention is to provide a thermal jacket for surrounding a container such as a wine bottle.

And still a further object of the invention is the provision of a flexible thermal jacket which can be folded for easy storage and transport.

And yet a further object of the invention is to provide an adjustable thermal jacket which can be securely fastened over beverage containers of various sizes.

And still a further object of the invention is the provision of thermal collars and jackets, according to the foregoing, which are relatively inexpensive to manufacture and comparatively simple and easy to use.

SUMMARY OF THE INVENTION

Briefly, to achieve the desired objects of the instant invention in accordance with the preferred embodiment thereof, various thermal wraps are provided for cooling an individual or a product. Each wrap comprises a fabric band having a thermally insulating outer layer and a non-insulating inner layer. A cavity is formed between the two layers for receiving a flexible cold pack containing deionized water and a chemical freezing agent.

In a first embodiment of the invention, the fabric band is in the form of a collar to be worn about an individual's neck or other body part. A strap at one end of the collar includes first fastening means for detachably and adjustably securing that end to the other end. One end is open to allow easy insertion and removal of the cold pack, so that the collar can be washed. Second fastening means are provided for closing the slit so that the cold pack remains in place when the collar is in use.

In a second embodiment of the invention, the fabric band is in the form of a jacket for surrounding a beverage container, such as a wine bottle. A flexible support member is attached to the bottom edge of the jacket for supporting the bottom of the container. Tightening means are provided in the top of the jacket for adjustably securing the jacket about containers of varying diameters.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which:

FIG. 1 is a perspective view showing an individual wearing a thermal collar according to a first embodiment of the invention.

FIG. 2 is a perspective view showing the thermal collar of FIG. 1 after removal from the individual.

FIG. 3 is a sectional view taken through line 3—3 of Fig. 2.

FIG. 4 is a fragmentary perspective view of the thermal collar of FIG. 1-3, with portions broken away and the cold pack insert partially withdrawn for greater clarity.

FIG. 5 is a fragmentary perspective view showing a sheet of the cold pack material used in the thermal collar of FIGS. 1-4.

FIG. 6 is a fragmentary perspective view showing an alternative embodiment of the thermal collar according to the present invention.

FIG. 7 is a perspective view, taken from the front, of a wine bottle encased in a thermal jacket according to a second embodiment of the invention.

FIG. 8 is a perspective view, taken from the bottom and front, of the bottle and jacket of FIG. 7 in exploded relation to one another.

FIG. 9 is a sectional view taken through line 9—9 of FIG. 8.

FIG. 10 is a perspective view of the thermal jacket of FIGS. 7-9, with the bottle removed and a portion broken away to reveal the cold pack.

FIG. 11 is a fragmentary view showing the top portion of a thermal jacket according to an alternative embodiment of the invention.

FIG. 12 is a fragmentary sectional view showing the bottom portion of a thermal jacket according to another alternative embodiment of the invention.

DETAILED DESCRIPTION OF THE PREFERRED EMBODIMENTS

Turning now to the drawings in which like reference characters indicate corresponding elements throughout the several views, attention is first directed to FIG. 1, which shows a thermal wrap according to the present invention, indicated in its entirety by the numeral 10. The thermal wrap is shown in the form of a collar worn around the neck 12 of an individual 14, but it may also be fastened about the forehead or at various locations along an arm or a leg or other body parts.

When used to cool an individual during exercise, the neck 12 is believed to be the most effective location for the collar 10, as most of an individual's heat loss occurs through the head and neck. However, when used to reduce pain in an injured body part, the collar 10 should be applied directly to the afflicted part.

The collar 10 comprises a fabric sleeve or band 14 having a thermally insulating outer layer 16 and a non-insulating inner layer 18. The outer layer 16 may be a two-ply material consisting of a plush, aesthetically pleasing outer surface resembling velour or velvet, and a backing formed from an insulating fabric or foil. The inner layer 18 is preferably a nylon mesh.

The band 14 includes a pair of opposite ends 20, 22 and a pair of edges 24, 26, which extend longitudinally between the ends 20, 22. One of the ends 22 includes an opening 28 which leads to a cavity 30 for containing a flexible cold pack insert 32. The opening 28 allows easy insertion and removal of the insert 32, so that band 14 can be washed in a conventional washing machine.

Cold pack inserts 32 are well known in the art and are readily available from commercial sources. One recommended insert is the product sold under the trademark "CRYOMAT" by Cryopak Corporation of Point Roberts, Washington. The "CRYOMAT" product, shown in FIG. 5, is marketed in the form of laminated plastic sheets 34, 36. A plurality of individually sealed compartments or pillows 38 are formed between the sheets 34, 36, preferably in rows and columns. Each compartment 38 is filled with a mixture 39 of deionized water and chemical freezing agents.

The compartmentalized configuration of the cold pack insert 32 makes it easy to fabricate the thermal collar 10 in a variety of lengths and widths to suit a variety of applications. To select the collar size, it is simply necessary to cut out a strip having a predetermined number of rows and columns of compartments 38. For use on an average sized neck, a strip having a width corresponding to two rows of compartments 38 is sufficient. The strip may then be doubled over as shown in FIG. 4, so that the final width of the collar 10 is approximately equal to the width of a single row. For application to parts of the body other than the neck, collars of greater width may be desirable.

To enable adjustment of the length of the collar 10 to fit individuals of different sizes, an elastic strap 40 is provided at one end 22 of the collar. First fastening means, such as a hook and loop type fastening strip 42, is secured to the free end of the strap 40. A mating strip may be provided on the opposite end 20 of the collar 10. However, if the outer layer 15 of the collar is fabricated from a material having sufficient roughness to allow, as in the illustrated case, the mating strip will not be necessary.

An alternative embodiment of the thermal collar, indicated in its entirety by the reference character 10A, is shown in FIG. 6. This embodiment is substantially the same as the previous embodiment, except that a longitudinally extending slit 44A is provided along one edge 26A of the collar. The slit 44A communicates with the opening 28A and the cavity 30A to facilitate insertion and removal of the cold pack 32A. Second fastening means, in the form of a zipper or hook and loop fastening strips 46A are provided for securing the slit 44A in a closed configuration so that the cold pack 32A remains in place while the collar 10A is in use. In addition, a flap 48A secured to one edge of opening 28A extends over the cold pack to prevent it from inadvertently sliding out of the opening 28A.

In addition to its manifestation as a collar, the thermal wrap according to the present invention may be manufactured in the form of a jacket 50 for chilling a product such as a beverage stored in a bottle 52 or other container, as illustrated in FIGS. 7-12.

Like the thermal collar 10, the thermal jacket 50 comprises a fabric sleeve or band 54 having an outer layer 56 formed of insulating material, an inner layer 58 formed of non-insulating material, and a cold pack insert 60. The width of the band 54, however, has been increased so that it covers at least half the height of the bottle 52. A band of lesser width could be used for chilling a smaller container such as a soft drink can.

The opposite ends 62, 64 of the band 54 are stitched together as shown in FIG. 9 to form a continuous annulus or tube for encircling the bottle 52. An elastic strap 66 is secured to diametrically opposed locations along the bottom edge 68 of the jacket 50 for supporting the bottom 70 of the bottle and to prevent the bottle from sliding out through the bottom of the jacket 50 when lifted. In addition, a drawstring 72 is provided along the top edge 74 to allow the jacket 50 to be tightened to conform to the necks of bottles of various sizes. Locking means, such as the illustrated barrel cord lock or pressure cinch mechanism 76, which is available from the John King Company of Los Angeles, Calif., may be provided to secure the drawstring 72 at the desired tension.

Two variations of the thermal jacket are shown in FIGS. 11 and 12. In the variation of FIG. 11, an elastic band 73A, rather than a drawstring, is used for tightening the upper edge 74A of the jacket 50A. In the variation of FIG. 12, the elastic bottom strap 66 of the previous embodiment is replaced with a flexible fabric floor 67B which entirely covers the bottom end of the jacket 50B. Like the band 54B from which the main body of the jacket 50B is constructed, the flexible floor 67B comprises an outer layer 56B formed of thermal insulating material and an inner layer 58B formed of non-insulating material, with a cold pack insert 60B disposed therebetween. The inclusion of the cold pack insert 60B in the flexible floor 67B results in less heat loss from the bottom of the bottle than in the embodiment of FIGS. 7 and 8.

Various other modifications and variations to the embodiments herein chosen for purposes of illustration will readily occur to those skilled in the art. To the extent that such variations and modifications do not depart from the spirit of the invention, they are intended to be included within the scope thereof which is assessed only by a fair interpretation of the following claims.

Having fully described and disclosed the instant invention and alternately preferred embodiments thereof in such clear and concise terms as to enable those skilled in the art to understand and practice the same, the invention claimed is:

1. A thermal wrap comprising:
   (a)
   a flexible band having
   an outer layer formed of thermal insulating material,
   an inner layer formed of non-insulating material,
   a pair of opposite ends,
   a pair of opposite edges extending longitudinally between said opposite ends,
   fastening means for securing said opposite ends to one another to form an annulus, and
   a cavity formed between said inner layer and said outer layer; and
   (b) a flexible cold pack carried within said cavity, said cold pack containing deionized water and a chemical freezing agent.

2. The thermal wrap according to claim 1, wherein said cold pack comprises a plurality of individually sealed compartments containing said deionized water and said chemical freezing agent.

3. The thermal wrap according to claim 1, wherein said fastening means comprises cooperating elements of a demountable fastener for detachably securing said opposite ends to one another.

4. The thermal wrap according to claim 3, wherein said cooperating elements comprise adjustment means for varying the size of said annulus.

5. The thermal wrap according to claim 1, wherein said fastening means comprises stitching for permanently securing said opposite ends to one another.

6. The thermal wrap according to claim 1, further comprising an opening formed in one of said ends and communicating with said recess to allow easy insertion and removal of said cold pack.

7. The thermal wrap according to claim 6, further comprising longitudinal slit means communicating with said opening and said recess for facilitating insertion and removal of said cold pack.

8. A thermal collar to be worn by an individual for cooling purposes, said collar comprising:
   (a)
   a flexible band for encircling a portion of said individual's body, said band including
   an outer layer for facing away from said individual's body,
   an inner layer for contacting said individual's skin,
   a pair of opposite ends,
   a pair of opposite edges extending longitudinally between said opposite ends,
   first fastening means for detachably securing said opposite ends to one another to form an annulus around said part of said individual's body, and
   a cavity formed between said inner layer and said outer layer; and
   (b) a flexible cold pack carried within said cavity.

9. The thermal collar according to claim 8, wherein said first fastening means comprises adjustment means for varying the size of said annulus.

10. The thermal collar according to claim 9, wherein said fastening means comprises:
    (a) an elastic strap secured to one end of said band, said strap having a free end; and
    (b) a hook and loop type fastener secured to the free end of said strap for cooperation with said outer layer of said band proximate the opposite end thereof.

11. The thermal collar according to claim 8, further comprising an opening formed in one of said ends and communicating with said recess to allow easy insertion and removal of said cold pack.

12. The thermal collar according to claim 11, further comprises flap means provided in said opening for preventing said cold pack from inadvertently sliding out of said recess.

13. The thermal collar according to claim 11, further comprising longitudinal slit means communicating with said opening and said recess for facilitating insertion and removal of said cold pack.

14. The thermal collar according to claim 13, further comprising second fastening means for securing said slit means in a closed configuration so that said cold pack remains in place when said collar is in use.

15. The thermal collar according to claim 8, wherein said outer layer comprises a thermal insulating material and said inner layer comprises a non-insulating material.

16. A thermal jacket for chilling a product stored within a container, said jacket comprising:
    (a)
    a flexible band for encircling said container, said band including
    an outer layer for facing away from said container, said outer layer being formed of thermal insulating material,
    an inner layer for contacting said container, said inner layer being formed of non-insulating material,
    a top edge,
    a bottom edge,
    a cavity formed between said inner layer and said outer layer; and
    (b) a flexible cold pack carried within said cavity.

17. The thermal jacket according to claim 16, further comprising support means secured to said bottom edge for supporting the bottom of said container.

18. The thermal jacket according to claim 17, wherein said support means comprises an elastic band having a pair of opposite ends, said ends being secured to diametrically opposed locations along said bottom edge.

19. The thermal jacket according to claim 17, wherein said support means comprises a flexible floor entirely covering the bottom of said container, said floor comprising:
 (a) an outer layer for facing away from said container;
 (b) an inner layer for contacting the bottom of said container;
 (c) a cavity formed between said inner layer and said outer layer; and
 (d) a cold pack carried within said cavity.

20. The thermal jacket according to claim 19, further comprising tightening means provided in said top edge for tightening said top edge to conform to containers of various sizes.

* * * * *